(12) United States Patent  
Gadberry et al.

(10) Patent No.: US 6,267,773 B1  
(45) Date of Patent: Jul. 31, 2001

(54) LOW PROFILE SURGICAL CLIP

(76) Inventors: Donald L. Gadberry, 33862 Mariana Dr., Apartment B, Dana Point, CA (US) 92629; Eric Lee, 125 Oxford, Irvine, CA (US) 92612

(*) Notice: Subject to any disclaimer, the term of this patent is extended or adjusted under 35 U.S.C. 154(b) by 0 days.

(21) Appl. No.: 09/353,413

(22) Filed: Jul. 15, 1999

(51) Int. Cl.$^7$ .................................................. A61B 17/08
(52) U.S. Cl. ............................................................ 606/151
(58) Field of Search ..................................... 606/151, 157, 606/158, 120; 29/243.56; 24/455, 456, 457, 458, 459, 460, 461

(56) References Cited

U.S. PATENT DOCUMENTS

| | | | |
|---|---|---|---|
| 3,509,882 | 5/1970 | Blake | 128/325 |
| 3,510,923 | 5/1970 | Blake | 24/263 |
| 4,106,508 | 8/1978 | Berlin | 128/346 |
| 4,337,774 | 7/1982 | Perlin | 128/325 |
| 4,424,811 | 1/1984 | Groot | 128/346 |
| 4,815,466 | 3/1989 | Perlin | 128/325 |
| 4,817,604 | 4/1989 | Smith, III | 128/346 |
| 4,931,058 | 6/1990 | Cooper | 606/158 |
| 4,932,955 | 6/1990 | Merz et al. | 606/158 |
| 4,976,721 | 12/1990 | Blasnik et al. | 606/157 |
| 5,011,487 | 4/1991 | Shichman | 606/158 |
| 5,042,118 | 8/1991 | Rubik | 24/523 |
| 5,335,398 | 8/1994 | Schöttker et al. | 24/528 |
| 5,653,720 | 8/1997 | Johnson et al. | 606/151 |
| 5,984,934 | * 11/1999 | Ashby et al. | 606/151 |

* cited by examiner

*Primary Examiner*—Henry J. Recla  
*Assistant Examiner*—Vy Q. Bui (57) ABSTRACT

A surgical spring clip includes a first molded component having a first jaw and a first finger tab. A second component having a second jaw and a second finger tab comprises the only other molded component. The first component has a telescoping relationship with the second component and is moveable by operation of the finger tab between a first position wherein the jaws are generally closed and a second position wherein the jaws are generally open. A spring disposed between the tabs and the jaws biases the first and second components toward the first position. The clip has a telescoping barrel with the general shape of a polygon in radial cross-section. An increased guidance link provides the clip with a guidance ratio of about 1.5 ratio. Alignment of the components is further enhanced by the provision of ramped projections and the accommodation of tolerances only along one side of the telescoping barrel. A simplified method of assembly requires movement of the second component through a window in the first component.

20 Claims, 8 Drawing Sheets

LOW PROFILE SURGICAL CLIP

BACKGROUND OF THE INVENTION

1. Field of the Invention

This invention relates generally to clips and clamps, and more specifically to low-profile spring clips adapted for use in surgical procedures.

2. Discussion of the Prior Art

Surgical clips and clamps are commonly used to occlude body conduits such as blood vessels. These clips and clamps typically have parallel jaws that are moveable between an open position and a closed position. Ratchet clips, such as those disclosed by Blake in U.S. Pat. No. 3,510,923, include a ratchet mechanism that functions to hold the jaws in the closed position. Other clips include extension or compression springs for biasing the jaws to the closed position. Representative of this art is U.S. Pat. No. 4,931,058. Low-profile clips include tabs, which are moveable to operate the jaws as disclosed by applicant in application Ser. No. 08/949,126, filed on Jun. 17, 1999, and entitled Low-Profile Surgical Clip, which is incorporated herein by reference.

The low-profile clips typically include a telescoping barrel with a pair of jaws on one side, and a pair of actuating finger tabs on the other. Closing the tabs opens the jaws against the bias of a spring disposed in the telescoping barrel. In the past, the telescoping barrels have been formed with a shape complimentary to that of the cylindrical spring. Although the cylindrical barrel design has facilitated assembly of the clip, unfortunately it has not contributed significantly to the angular stability of the jaws. As a consequence, the jaws have tended to scissor, rather than maintain their preferred parallel relationship.

The guidance ratios of the telescoping barrels has also been somewhat limited in the past. This guidance ratio is commonly determined by dividing the guidance length by the radial width of the smallest telescoping member. In the past, guidance ratios for a low-profile construction have been generally limited to about 1.0.

Of course, it is always desirable to achieve an improved construction requiring a fewer number of parts. Where this can occur in combination with an easier method of assembly, manufacturing costs can be greatly reduced. It is always desirable to decrease the flexibility of a clip in order to prevent scissoring and to maintain the desired parallel relationship of the jaws. Providing increased guidance ratios is also desirable.

SUMMARY OF THE INVENTION

In accordance with the present invention, the deficiencies of the prior art have been overcome with a clip assembly, including only two molded components. While maintaining the desired telescoping relationship of the barrel, the barrel parts can be formed with a cross-sectional shape in the form of a polygon, such as a rectangle. This greatly increases the stability of the clip and the desired parallel relationship of the jaws. This stability is further increased by developing a guidance ratio greater than about 1.5, and by providing ramped projections between the telescoping parts in order to minimize jaw tipping. A rectangular barrel configuration also facilitates a method of assembly which does not require that the parts be snap-fit and yet facilitates accurate alignment and stability for the clip.

In one aspect of the invention, the surgical spring clip includes a first molded component having a first jaw and a first finger tab. A second component having a second jaw and second finger tab comprises the only other molded component of the clip. The first component is moveable by operation of the first finger tab between a first position wherein the jaws are generally closed and a second position wherein the jaws are generally open. The spring is disposed generally between the tabs and the jaws for biasing the first component and the second component toward the first position.

In another aspect of the invention, a surgical spring clip includes a first component having a first barrel, with a first finger support disposed on one side of the barrel and a first jaw disposed on an opposing side of the barrel. A second component has a second barrel with a second finger support disposed on one side of the second barrel and a second jaw disposed on an opposing side of the second barrel. The first barrel and second barrel have a telescoping relationship and are moveable relative to each other between first position and a second position. At least one of the first barrel and the second barrel define a housing. A spring having a cross-sectional shape is disposed in the housing for biasing the first barrel and the second barrel to the first position. The first barrel and second barrel have a cross-sectional shape which is different than the cross-sectional shape of the spring.

In a further aspect of the invention, a method for assembling a surgical spring clip includes the steps of providing a first component having a first barrel with a first finger support on one side of the first barrel and a first jaw on the opposite side of the first barrel. Similarly, a second component has a second barrel with a second finger support on one side of the second barrel and a second jaw on the opposite side of the second barrel. A window is formed in the first component between a first wall and a second wall parallel to the first wall. The second jaw of the second component is moved generally parallel to the first wall and the second wall of the first component and into the window. During this moving step, the second component is tilted relative to the first component to place the first jaw and the second jaw in a generally parallel relationship. Also, during this moving step, a spring can be installed between the first component and the second component.

These and other features and advantages of the invention will become more apparent with a discussion of preferred embodiments in reference to the associated drawings.

DESCRIPTION OF THE DRAWINGS

FIGS. 8–10 illustrate steps in a preferred method for assembling the clip of FIG. 1;

DESCRIPTION OF PREFERRED EMBODIMENTS AND BEST MODE OF THE INVENTION

Figure 1:
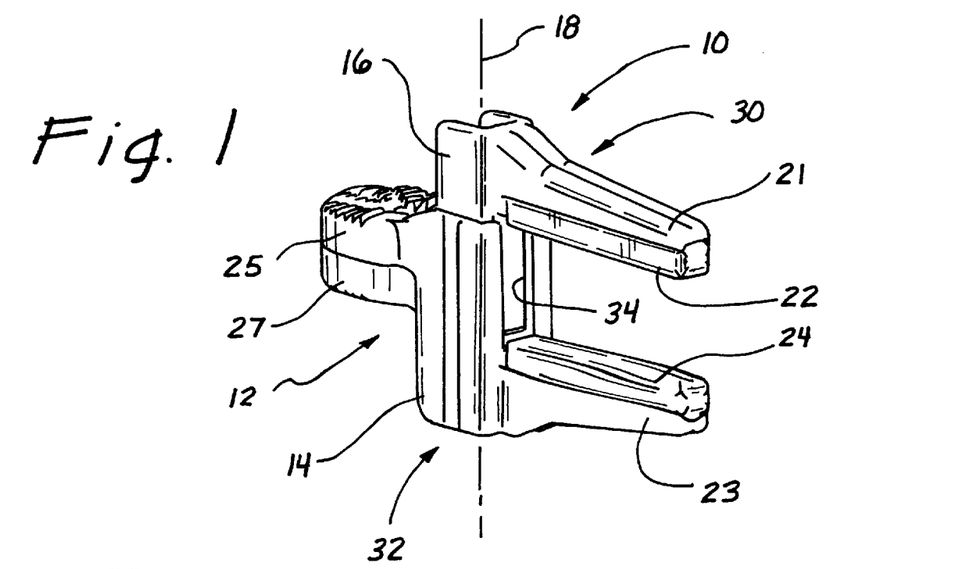
FIG. 1 is a front/side-perspective view of a preferred embodiment of the clip of the present invention.

A low-profile surgical spring clip is illustrated in FIG. 1 and designated generally by the reference numeral 10. The clip 10 includes a telescoping barrel 12 formed with an outer barrel portion 14 moveable along an axis 18 relative to an inner barrel portion 16. Extending on one side of the barrel 12 are a pair of jaws 21 and 23, which are moveable between a generally open state and a generally closed state. On the opposite side of the barrel 12, a pair of finger supports or tabs 25 and 27 can be provided to facilitate engagement with a clip applier (not shown) or the fingers (not shown) of a user. In the illustrated embodiment, atraumatic inserts 22 and 24 are attached to the jaws 21 and 23, respectively.

Figure 2:
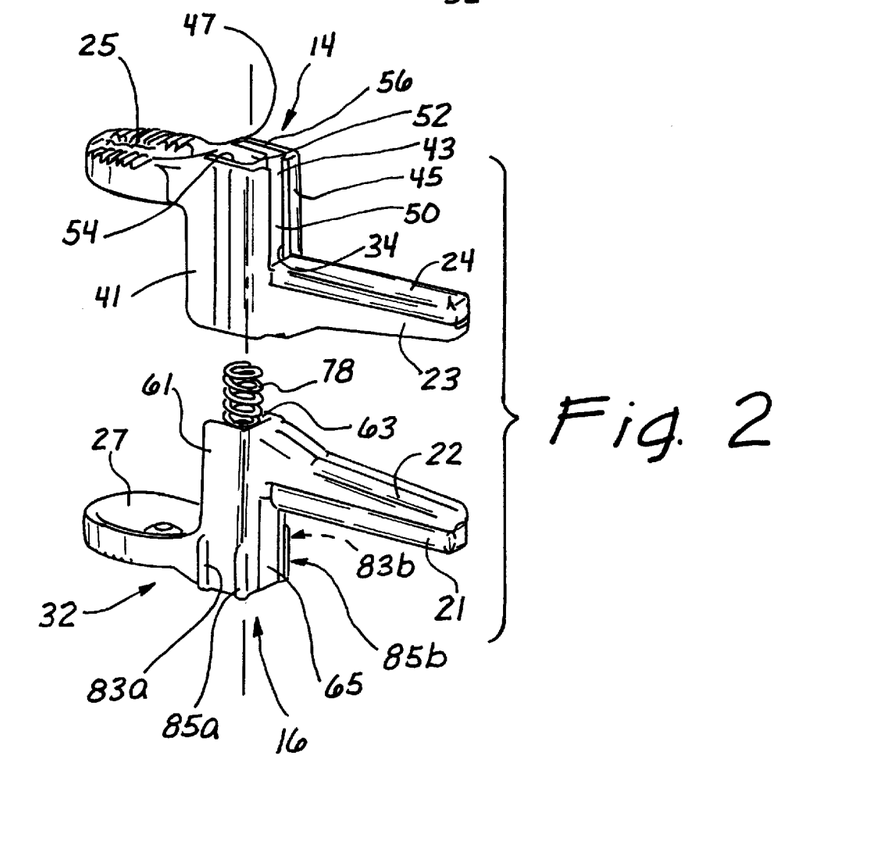
FIG. 2 is a front/side exploded view of the clip illustrated in FIG. 1, showing the two molded components of the clip axially separated.
Figure 3:
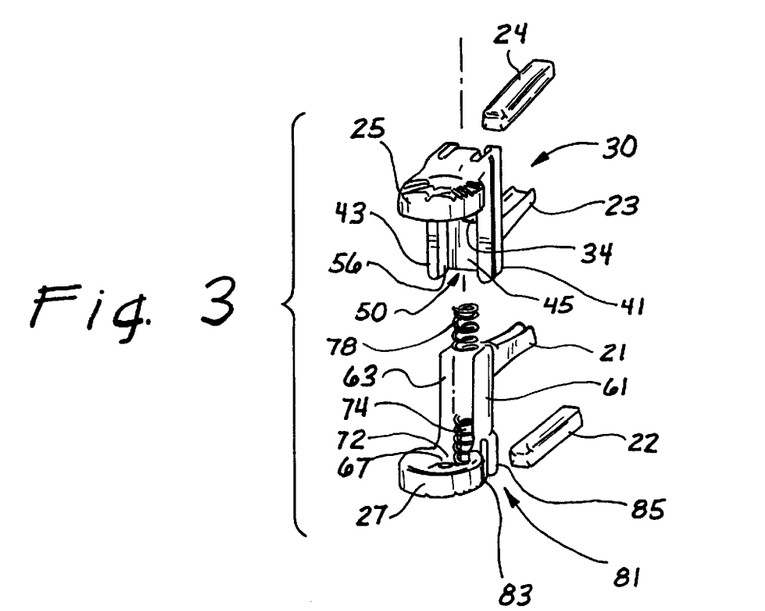
FIG. 3 is an exploded view of the clip illustrated in FIG. 1, showing a preferred position for a compression spring.

It is of particular advantage that the clip 10 of this embodiment can be formed with only two molded components. A first component 30 will typically include the jaw 21, the inner barrel portion 16, a first spring stop 72 as shown in FIG. 3, and the finger tab 27, while a second component 32 includes the jaw 23, the outer barrel portion 14, a second spring stop 52 as shown in FIG. 2, and the finger tab 25. With this configuration, the second component 32 includes the bottom jaw 23 and the top finger tab 25. The first component 30 includes the top jaw 21 and the bottom finger tab 27. A window 34 is formed in the front side of the outer barrel portion 14 and extends generally parallel to the axis 18. This window 34 is configured to accommodate movement of the jaw 21 relative to the jaw 23.

The configuration of the telescoping barrel portions 14 and 16 are of particular interest to this embodiment. These structures are best illustrated in the front side view of FIG. 2 and the back side view of FIG. 3 where the first and second components 30 and 32, respectively, are axially separated. The outer barrel portion 14 includes a pair of side walls 41 and 43 and a front wall 45, portions of which define the window 34. A back wall 47 extends only a short distance downwardly and generally parallel to the front wall 45.

The walls 41, 43, 45, and 47 in this embodiment have a polygonal configuration in radial cross-section. For example, in the illustrated embodiment, the side walls 41 and 43 are generally parallel to each other and generally perpendicular to the front wall 45 and back wall 47. Thus, in this embodiment the polygonal shape of the outer barrel portion 14 is generally rectangular or square.

Figure 5A:
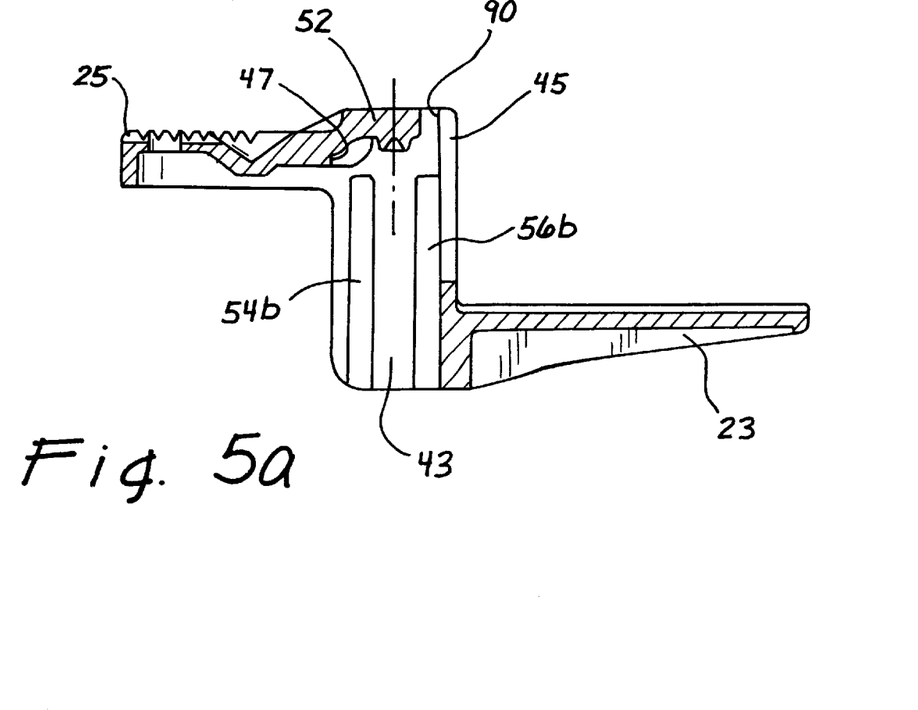
FIG. 5a is a cross-section view taken along lines 5a—5a of FIG. 4.
Figure 5B:
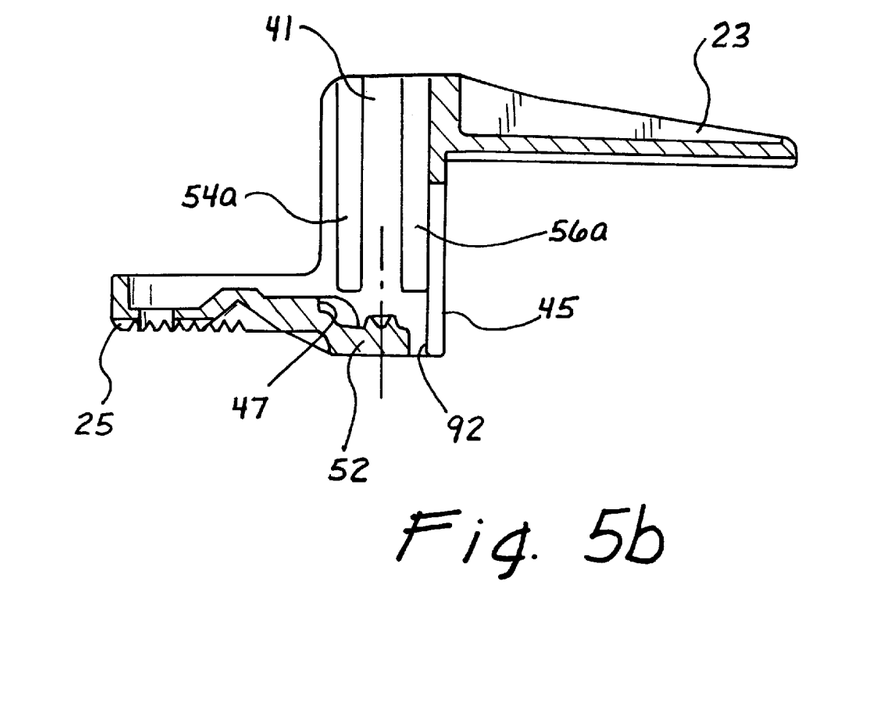
FIG. 5b is a cross-section view taken along lines 5b—5b of FIG. 4.

In combination, the walls 41, 43, 45, and 47 define a housing or cavity 50. Since the back wall 47 extends downwardly only a short distance, the back of the cavity 50 is generally open, as best illustrated in FIG. 3. The cavity 50 is further characterized by a ceiling flange, or second spring stop 52 that cantilevers from the back wall 47 toward the front wall 45. This flange 52 forms a U-shaped space with the adjacent walls 41, 43, and 45. The cavity 50 is further defined by a pair of guide slots 54a and 56a that extend inwardly from the side wall 41, and a pair of guide slots 54b and 56b that extend inwardly from the side wall 43. The guide slots 54a, 56a and 54b, 56b, which are best illustrated in the respective views of FIGS. 5b and 5a, are collectively referred to herein as the guide slots 54 and 56.

The inner barrel portion 16 of the second component 32 can be similarly provided with side walls 61 and 63, a front wall 65, and a back wall 67. In order to mate with the outer barrel portion 14, the side walls 61 and 63 of this embodiment are preferably parallel, and perpendicular to the front wall 65 and the back wall 67. In combination, these walls 61, 63, 65, and 67 form an interior housing or cavity 70, which is further defined by a floor 72, or first spring 72 stop that extends between the front wall 65 and back wall 67. A support post 74, best illustrated in FIG. 3, extends axially of the floor 72 within the cavity 70. In this embodiment, the back wall 67 extends only a short distance upwardly and generally parallel to the front wall 65. This provides a large area of access into the cavity 70 at the back of the barrel portion 16.

As noted, the inner barrel portion 16 is sized and configured to fit within the cavity 50 of the outer barrel portion 14. Operation of the clip 10 is facilitated by a close sliding and telescoping relationship between the outer surfaces of the inner barrel walls 61, 63, and 65, and the inner surfaces of the outer barrel walls 41, 43, and 45. When the first component and the second component are assembled, a compression spring 78 can be mounted on the post 74, where it is supported between the floor 72 of the inner barrel portion 16 and the ceiling flange 52 of the outer barrel portion 14.

A pair of guide ribs 83a and 85a, which extend from the outer surface of the side wall 61, and a pair of guide ribs 83b and 85b, which extend from the outer surface of the side wall 63, are collectively referred to herein as the guide ribs 83 and 85. When the clip 10 is assembled, the guide ribs 83a and 85a of the inner barrel portion 16 slide within the associated guide slots 54a and 56a of the outer barrel portion 14. Similarly, the guide ribs 83b and 85b of the inner barrel portion 16 slide within the associated guide slots 84b and 86b of the outer barrel portion 14. In a manner discussed in greater detail below, these slots 54 and 56, and the associated ribs 83 and 85, contribute greatly to the desired telescoping relationship of the barrel portions 14 and 16, and the generally parallel relationship of the jaws 21 and 23.

Figure 4:
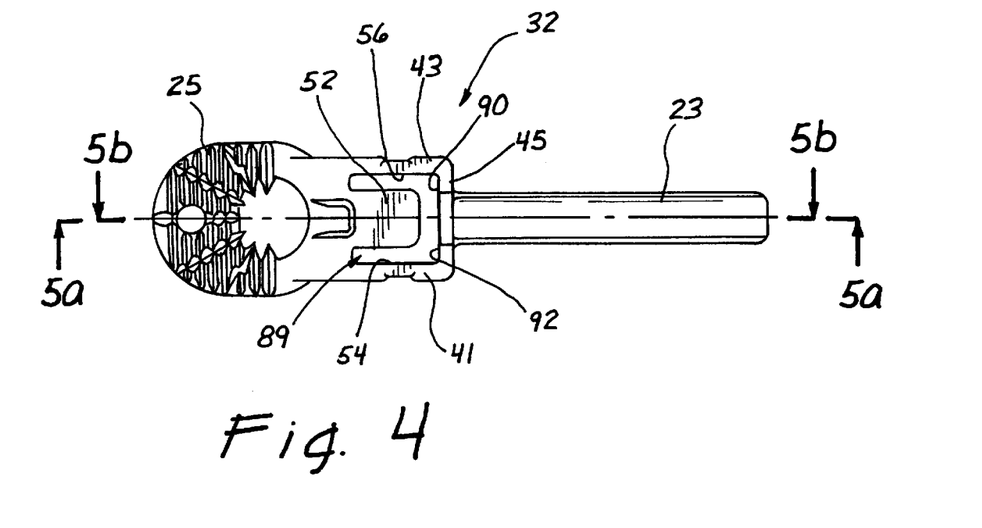
FIG. 4 is a top plan view of an outer component of the clip illustrated in FIG. 1.

The first component 30, including the outer barrel portion 14, is further illustrated in the detailed views of FIGS. 4, 5a, and 5b. In the top plan view of FIG. 4, it can be seen that the ceiling flange 52 forms a U-shaped slot 89 with the walls 41, 43, and 45. In FIG. 5a, the guide slots 54b and 56b are detailed, along with a projection 90 that extends inwardly into the cavity 50 from the front wall 45. Similarly, in FIG. 5b, the guide slots 54a and 56a are detailed along with a projection 92 that extends inwardly into the cavity 50 from the front wall 45. These projections 90, 92 facilitate alignment of the jaws 21 and 23 in a manner discussed in greater detailed below. The back wall 47 is best illustrated in the cross-section view of FIGS. 5a and 5b.

Figure 6:
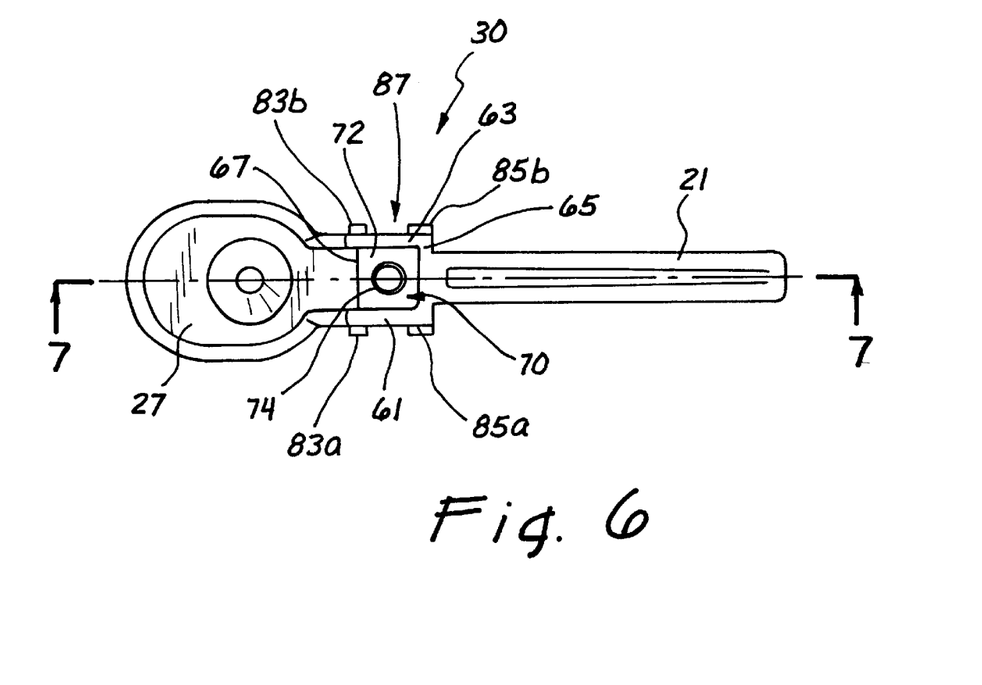
FIG. 6 is a top plan view of an inner component of the clip illustrated in FIG. 1.
Figure 7:
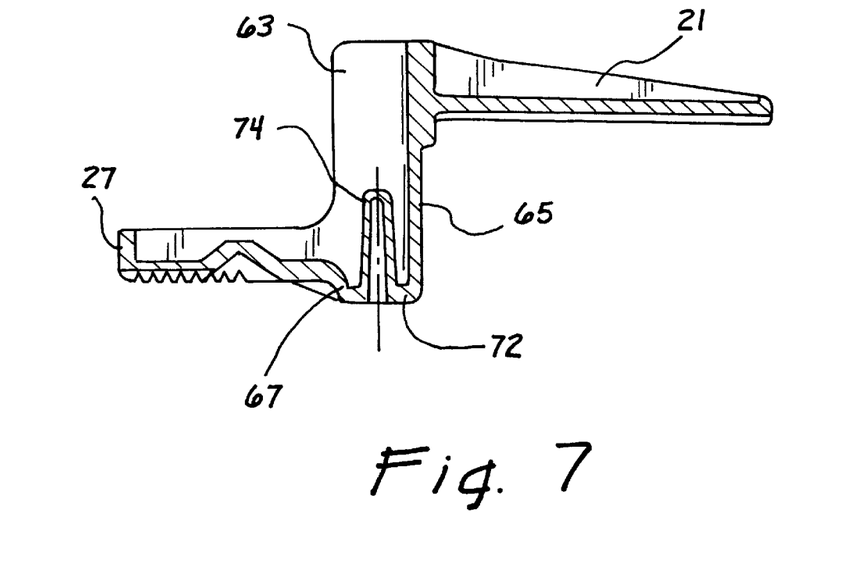
FIG. 7 is a cross-section view taken along lines 7—7 of FIG. 6.

Detailed views of the second component, including the inner barrel portions 16, are illustrated in FIGS. 6 and 7. Of particular interest in FIG. 6 is the back wall 67 that defines with the walls 61, 63, and 65, the housing or cavity 70. The post 74 is best illustrated in the cross-section view of FIG. 7.

Figure 8:
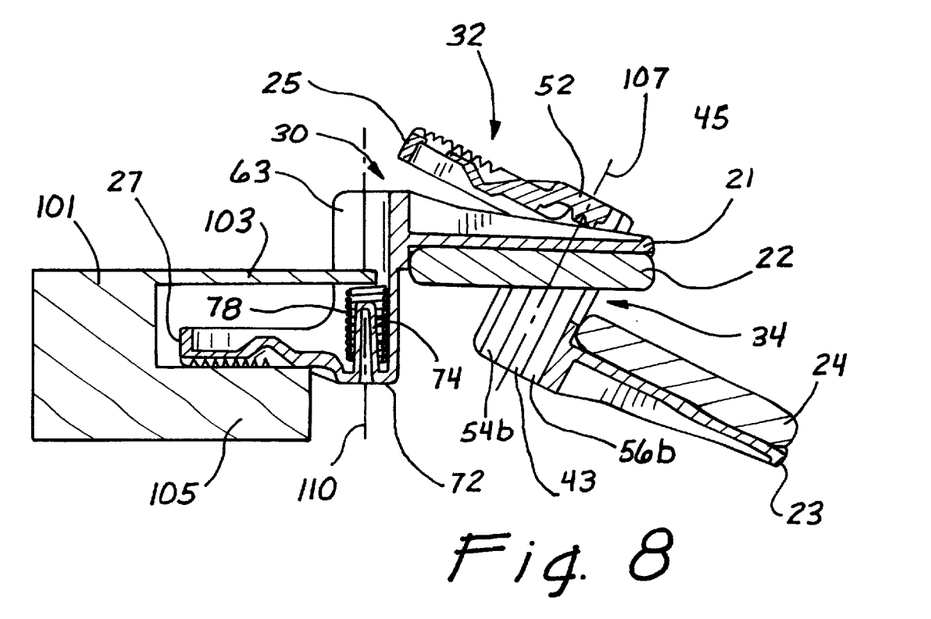
FIG. 8 is a side elevation view illustrating one of the clip components being inserted through a window in the other of the clip components.
Figure 9:
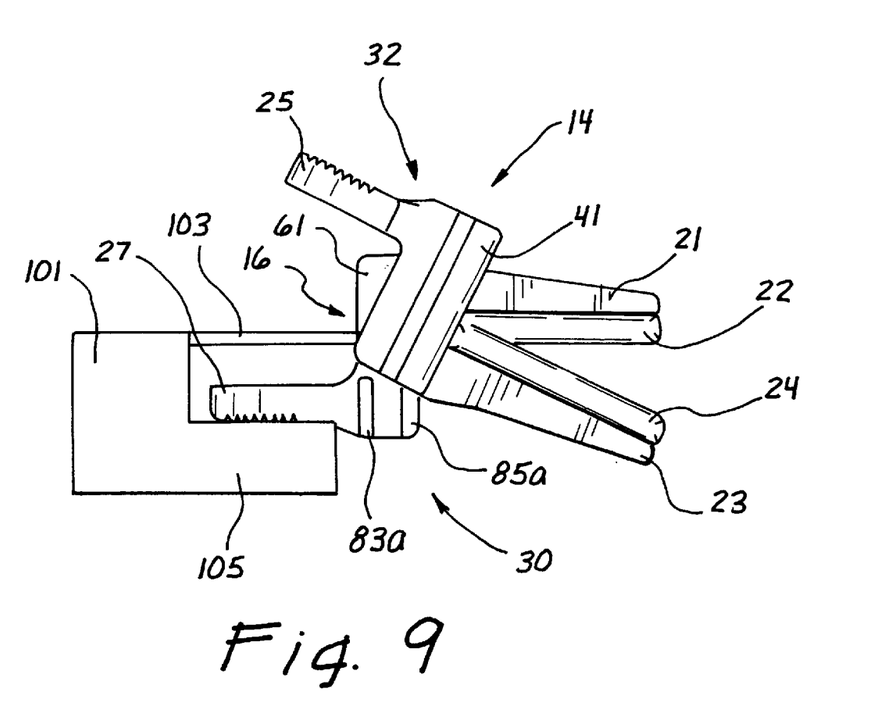
FIG. 9 illustrates a step for aligning a slot and a rib during a tilting step of the assembly process.
Figure 10:
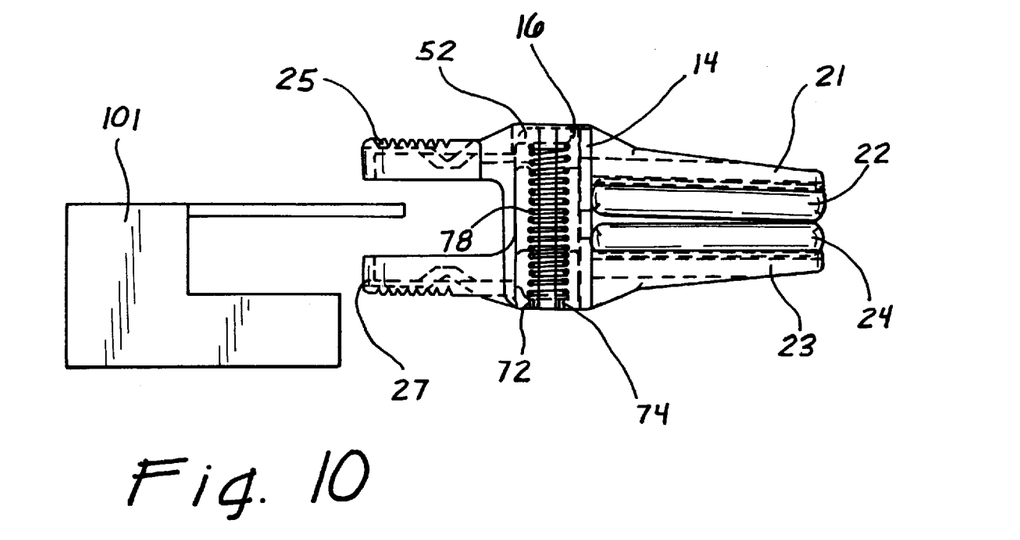
FIG. 10 is a cross-section view illustrating the clip in an assembled state with the spring operatively disposed between components of a telescoping barrel.

Having discussed the first component 30 and second component 32 in detail, one can better understand a preferred method of assembly that is illustrated in FIGS. 8–10. In order to facilitate this assembly process, a jig 101 can be provided with two generally parallel flanges 103 and 105. This jig 101 is particularly beneficial in mounting the compression spring 78 between the ceiling flange 52 of the first component 30 and the floor 72 of the second component 32.

Initially, the spring 78 can be positioned on the post 74 of the second component 32. Then, the top of the spring 78 can be engaged by the flange 103 as the second component 32 is tilted into the jig 101. With the flanges 103 and 105 suitably spaced, the spring 78 is compressed with the bottom flange 105 supporting the bottom of the barrel portion 16, and the top flange 103 extending over the compressed spring 78. With the second component 32 thus mounted as illustrated in FIG. 8, the first component 30 can be moved into proximity with the second component 32.

In accordance with a preferred method, the first component 30, with the outer barrel portion 14 on an axis 107, is moved onto the second component 32, with the inner barrel portion 16 on an axis 110. Initially, the jaw 21 of the first component 30 is inserted into the window 34 of the second component 32. As the two components 30 and 32 are moved into further relative proximity, the bottom of the guide slots 54a, 56a, 54b, and 56b of the first component 30 can be moved onto the associated guide ribs 83a, 85a, 83b, and 85b of the second component 32. Further movement of the first component 30 toward the second component 32 will tilt the first component 30 and begin to align the axis 107 and 110 as the jaws 21 and 23 approach the desired parallel relationship. As the first component 30 is tilted, the guide ribs 83a, 85a, 83b, and 85b are moved into the associated slots 54a, 56a, 54b, and 56b, as illustrated in FIG. 9.

With this embodiment of the clip 10, movement of the first component 30 relative to the second component 32 must be with an orientation and direction dictated by the parallel relationships of the side walls 41, 43 and 61, 63. Accordingly, this step is accomplished in a preferred method with the jaws 21 and 23 in a non-parallel relationship, but nevertheless extending in a single vertical plane. With this orientation, the walls 41, 43, and 61, 63 will be parallel, not only with respect to each other, but also with respect to the vertical plane.

Once the axis 107 of the second component 32 is aligned with the axis 110 of the first component 30, the clip 10 can be removed from the jig 101. In this step of the process, the spring 78 is free to expand between the floor 72 of the second component and the ceiling flange 52 of the first component 30. As illustrated in FIGS. 8–10, the assembly process can be accomplished with the inserts 22 and 24 mounted on the associated jaws 21 and 23. Alternatively, the inserts 22 and 24 can be mounted after the clip 10 is removed from the jig 101.

Figure 11:
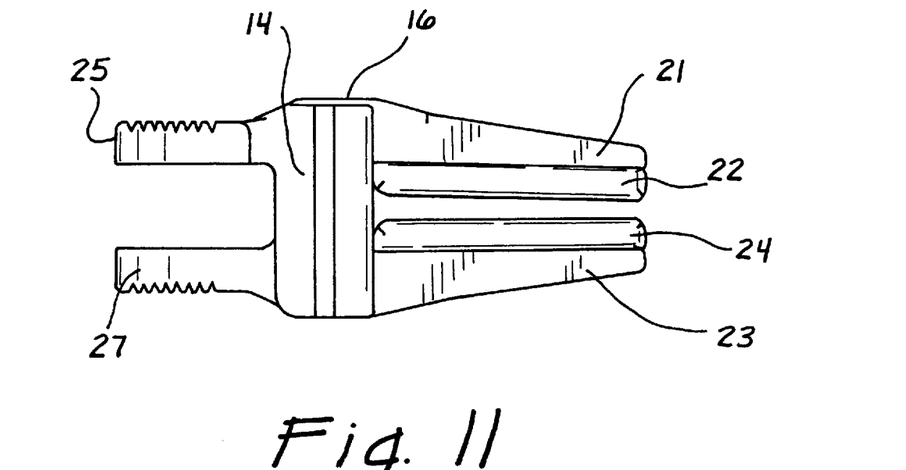
FIG. 11 is a side elevation view of the assembled clip with the jaws in close proximity, the view showing the jaws in an accentuated non-parallel relationship.
Figure 12:
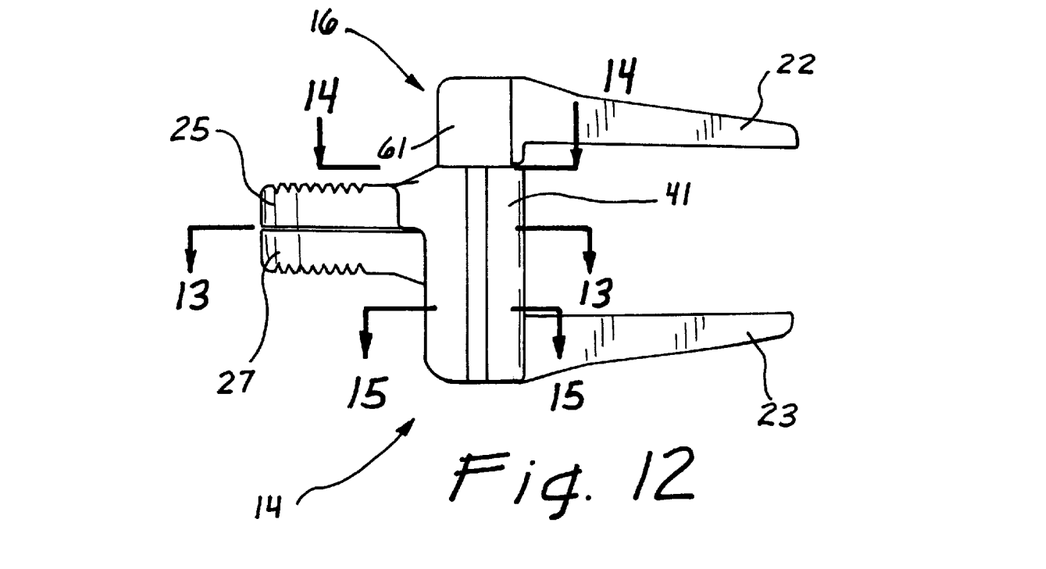
FIG. 12 is a side elevation view of the clip in an assembled state with the finger tabs compressed and the jaws in the open state, with a protrusion between the telescoping barrel portions facilitating a desired, generally parallel relationship of the jaws.
Figure 13:
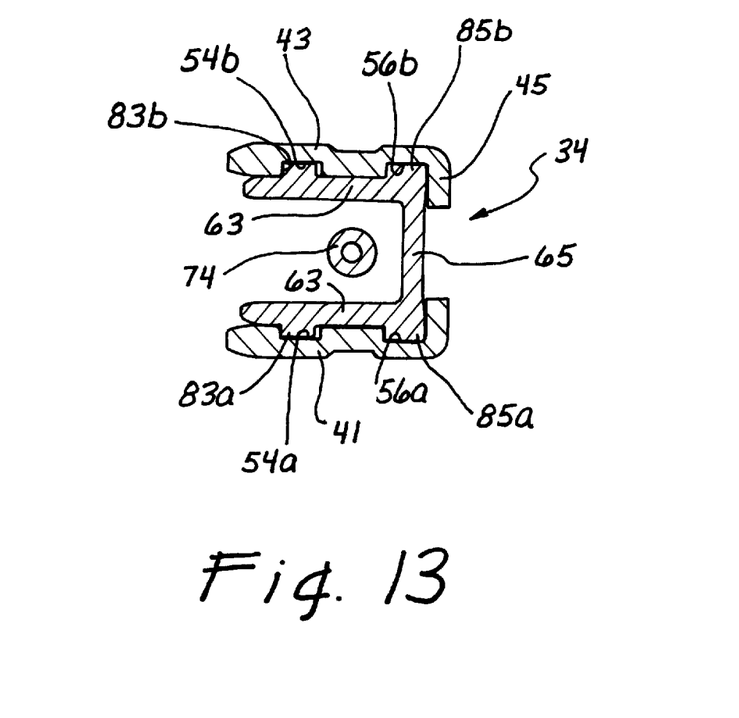
FIG. 13 is a cross-section view taken along lines 13—13 of FIG. 12 and illustrating the absence of a protrusion between the telescoping barrel portions.

Once the clip 10 has been assembled, it is operable, by movement of the tabs 25 and 27, between a closed position, illustrated in FIG. 10, and an open position, illustrated in FIG. 11. In the open position, the tabs 25 and 27 are moved into proximity against the bias of the spring 78 to separate the jaws 21 and 23. As the tabs are being forced into proximity, the telescoping barrel 12 tends to function as a fulcrum, causing the tips of the jaws 21 and 23 to tilt toward each other. Thus, the normal operation of a low-profile clip can tend to drive the jaws into an undesirable, non-parallel relationship. It has been found that this tendency is further accommodated by the normal tolerances that exist between the outer and inner barrel portions 14 and 16, respectively. These tolerances are best illustrated in the cross-section view of FIG. 13.

Figure 14:
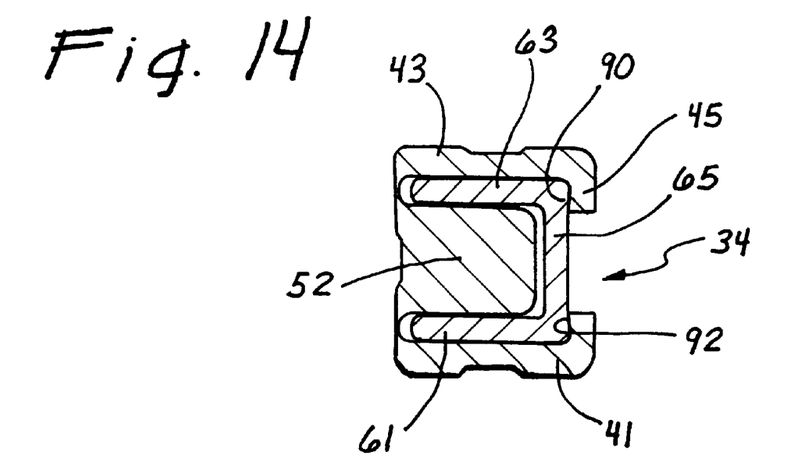
FIG. 14 is a cross-section view taken along lines 14—14 of FIG. 12 and illustrating the presence of the protrusion between the telescoping barrel portions.

In order to inhibit the tilting tendencies of the jaws 21 and 23, the preferred embodiment includes a pair of projections which protrude into the cavity 70 from the uppermost points of the front wall 45 associated with the first component 30. As illustrated in FIG. 14, these protrusions 90 and 92 tend to force the front wall 65 of the second component 32 away from the inner surface of the front wall 45. Since this occurs only at the upper regions of the front wall 45, the entire inner barrel portion 16 is tilted backwardly within the cavity 70, so that the jaws 21 and 23 can maintain the desired parallel relationship.

Figure 15:
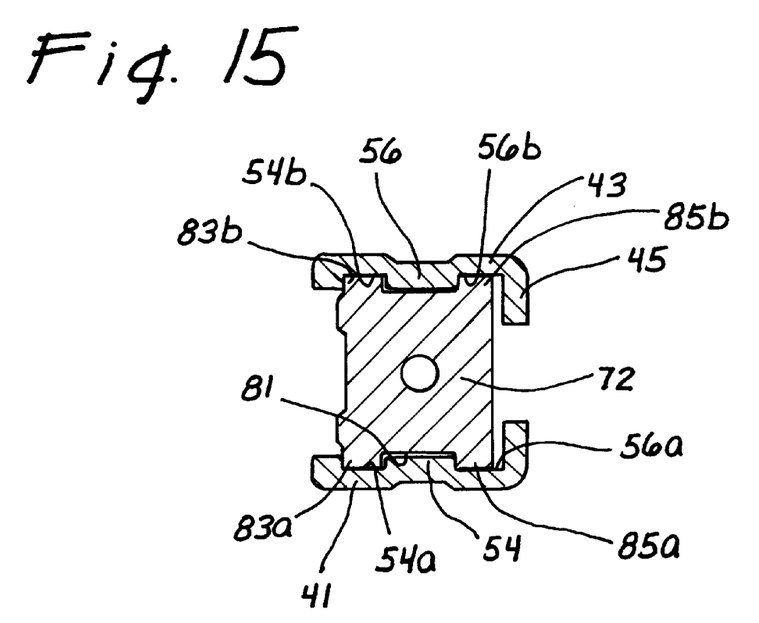
FIG. 15 is a cross-section view taken along lines 15—15 of FIG. 12 and illustrating a gap accommodating component tolerances on only one side of a pair of guidance ribs.

This desired parallel relationship is further enhanced by controlling the tolerances associated with the guide ribs 83 and 85 and the associated guide slots 54 and 56. These tolerances are best illustrated in the cross-section view of FIG. 15, where it will be noted that the ribs 83a and 85a are configured with substantially zero tolerance at the back side of guide slots 54a and 56a and a positive tolerance at the front side of the slots 54a and 56a. In a similar manner, the opposing guide ribs 83b and 85b are provided with substantially zero tolerance along their rearward edges and a positive tolerance along their forward edges. By thus controlling the orientation of the guide ribs 83 and 85, the first and second components 30, 32 will only have tolerances that accommodate the desired parallel relationship between the jaws 21 and 23.

Another feature of the present invention is associated with the guidance ratio of the telescoping barrel portions 14 and 16. This ratio is a function of the guidance length along the axis 18, divided by the width of the smallest telescoping member such as the inner barrel portion 16. In a preferred embodiment, this width is about 0.223 inches, while the guidance length is about 0.375 inches. As a result, a highly desirable guidance ratio of about 1.7 is achieved. This further insures the alignment of the axes 107 and 110 associated with the respective telescoping barrel portions 14 and 16. When these axes 107 and 110 are aligned, the jaws 21 and 23 have the desired parallel relationship.

Given the exemplary embodiments of the invention have been shown and described, many other changes, modifications, and substitutions will now be apparent to those of ordinary skill in the art, which do not necessarily depart from the spirit and scope of this invention as set forth in the following claims.

What is claimed is:

1. A surgical spring clip, including:
   a first one-piece molded component having a first jaw, a first spring stop and a first finger tab;
   a second one-piece molded component comprising the only other additional molded component, and having a second jaw, a second spring stop and a second finger tab;
   the first component having a telescoping relationship with the second component and being moveable by operation of the finger tabs between a first position wherein the jaws are generally closed and a second position wherein the jaws are generally open; and a spring disposed between the tabs and the jaws and between the first spring stop and the second spring stop for biasing the first component and the second component toward the first position.

2. The surgical spring clip recited in claim 1, further comprising:

a first barrel portion included in the first component;

a second barrel portion included in the second component;

the first barrel portion having a telescoping relationship with the second barrel portion and defining a housing sized and configured to receive the spring.

3. The surgical spring clip recited in claim 2 wherein at least one of the first barrel portion of the second barrel portion defines a window disposed between the tabs and providing access for the spring into the housing.

4. The surgical spring clip recited in claim 2 wherein the first barrel portion and the second barrel portion have a general shape of a polygon in radial cross-section.

5. The surgical spring clip recited in claim 4 wherein the polygon is a rectangle.

6. The surgical spring clip recited in claim 2, wherein:

the first barrel portion has a first width;

the second barrel portion has a second width less than the first width;

the first barrel portion being in telescopic engagement with the second barrel portion over a particular length between the first position and the second position; and the particular length is greater than 1½ times the second width.

7. The surgical spring clip recited in claim 2, wherein:

the first component and the second component are in sliding engagement between the inner surface of the second barrel portion and the outer surface of the first barrel portion; and the clip further comprises a projection extending inwardly of the inner surface of the first barrel portion for facilitating the generally parallel relationship between the first jaw and the second jaw.

8. The surgical spring clip recited in claim 2, wherein:

the first component and the second component are in sliding engagement between the inner surface of the second barrel portion and the outer surface of the first barrel portion; and the second barrel portion includes a protrusion extending toward the outer surface of the first barrel portion.

9. The surgical spring clip recited in claim 1 wherein the first spring stop comprises a floor.

10. The surgical spring clip recited in claim 1 wherein the second spring stop comprises a ceiling flange.

11. A surgical spring clip, including:

a first molded component having a first barrel with a first finger support and a first spring stop disposed on one side of the barrel and a first jaw disposed on an opposing side of the barrel;

a second molded component comprising the only other additional molded component, and having a second barrel with a second finger support and a second spring stop disposed on one side of the second barrel and a second jaw disposed on an opposing side of the second barrel;

the first barrel and the second barrel having a telescoping relationship and being moveable relative to each other between a first closed position and a second open position, at least one of the first barrel and the second barrel defining a housing;

a spring having a cross-sectional shape and being disposed in the housing between the first spring stop and the second spring stop for biasing the first barrel and the second barrel toward the first closed position; and the first barrel and second barrel having a cross-sectional shape different than the cross-sectional shape of the spring.

12. The surgical spring clip recited in claim 11, wherein:

the cross-sectional shape of the spring is a circle; and the cross-sectional shape of the first barrel and the second barrel is a polygon.

13. The surgical spring clip recited in claim 12 wherein the polygon is a rectangle.

14. The surgical spring clip recited in claim 11 wherein the first barrel has a first radial width and a telescoping relationship with the second barrel along an axial telescoping length; and the axial telescoping length is greater than 1½ times the radial width of the first barrel.

15. The surgical spring clip recited in claim 11, wherein:

the tabs have finger engagement points disposed at a first distance from the spring and applier engagement points disposed at a second distance from the spring; and the second distance being less than the first distance from the spring.

16. The surgical spring clip recited in claim 11 wherein the first spring stop comprises a floor.

17. The surgical spring clip recited in claim 11 wherein the second spring stop comprises a ceiling flange.

18. A method for assembling a surgical spring clip, comprising the steps of:

providing a first component having a first barrel, a first tab on one side of the first barrel and a first jaw on the opposite side of the first barrel;

providing a second component having a second barrel, a second tab on one side of the second barrel and a second jaw on the opposite side of the second barrel;

forming a window in the first component between a first wall and a second wall parallel to the first wall;

moving the second jaw of the second component generally parallel to the first wall and the second wall of the first component, and into the window; and during the moving step tilting the second component relative to the first component to place the jaws in a generally parallel relationship; and installing a spring between the first component and the second component.

19. The surgical spring clip recited in claim 18, wherein:

the first providing step includes the step of providing the first component with a guide slot; and the second providing step includes the step of providing the second component with a guide rib; and the tilting step includes the step of moving the guide rib into the guide slot.

20. The method recited in claim 18 wherein the installing step includes the step of positioning the spring between the first component and the second component, and between the first wall and the second wall of the first component.

* * * * *